United States Patent [19]

Okano et al.

[11] Patent Number: 5,116,702
[45] Date of Patent: May 26, 1992

[54] ELECTROPHOTOGRAPHIC LIGHT-SENSITIVE MATERIAL COMPRISING A CHARGE GENERATING LAYER AND A CHARGE TRANSFER LAYER

[75] Inventors: Sadao Okano; Kazuya Hongo, both of Kanagawa, Japan; Hidekazu Aonuma, Ontario, Canada; Hiroshi Miyamoto, Kanagawa, Japan

[73] Assignee: Fuji Xerox Co., Ltd., Tokyo, Japan

[21] Appl. No.: 529,361

[22] Filed: May 29, 1990

[30] Foreign Application Priority Data

May 30, 1989 [JP] Japan .................................. 1-134751
May 30, 1989 [JP] Japan .................................. 1-134753

[51] Int. Cl.$^5$ ............................................. G03G 5/09
[52] U.S. Cl. ...................................... 430/54; 430/83; 430/126
[58] Field of Search ...................... 430/83, 58, 91, 54, 430/126

[56] References Cited

U.S. PATENT DOCUMENTS 4,362,801 12/1982 Yagishita et al. ...................... 430/83
4,417,060 11/1983 Czerney et al. ........................ 430/83

*Primary Examiner*—John Goodrow
*Attorney, Agent, or Firm*—Finnegan, Henderson, Farabow, Garrett and Dunner

[57] ABSTRACT

An electrophotographic light-sensitive material is disclosed, which comprises a conductive support having formed thereon, in succession, a charge generating layer and a charge transfer layer, wherein the charge generating layer comprises a binder resin containing therein a positive hole-transferring charge generating pigment and a specific dicyanovinyl compound or coumarin compound. An image forming process using the electrophotographic light-sensitive material is also disclosed.

7 Claims, 1 Drawing Sheet

ELECTROPHOTOGRAPHIC LIGHT-SENSITIVE MATERIAL COMPRISING A CHARGE GENERATING LAYER AND A CHARGE TRANSFER LAYER

FIELD OF THE INVENTION

This invention relates to an electrophotographic light-sensitive material comprising an electrically conductive support having formed in succession thereon a charge generating layer and a charge transfer layer. The invention also relates to an image forming process using the electrophotographic light-sensitive material.

BACKGROUND OF THE INVENTION

Hitherto, for an electrophotographic light-sensitive material, an inorganic photoconductive material such as selenium, selenium alloy, zinc oxide, cadmium sulfide etc., has been mainly used. However, in the electrophotographic light-sensitive materials using the inorganic photoconductive materials, there are problems in the points of producibility, production cost, flexibility of the light-sensitive material, etc.

Recently, for solving the problems accompanying the inorganic photoconductive materials, there are known electrophotographic light-sensitive materials using organic photoconductive materials such as polyvinylcarbazole-2,4,7-trinitrofluorenone (TNF). Furthermore, recently, laminated layer-type electrophotographic light-sensitive materials formed by the combination of one or more kinds of pigments such as perylene series pigments, perinone series pigments, phthalocyanine series pigments, azoic pigments, etc., or dyes such as cyanine dyes, pyrylium salt dyes, thiapyrylium salt dyes, squarylium salt dyes, etc., as charge generating materials and one or more kinds of charge transfer materials such as pyrazoline, hydrazone, triallylamine, stilbene, etc., are proposed as disclosed in JP-A-58-16247 (the term "JP-A" as used herein means an "unexamined published Japanese patent application").

However, the electrophotographic light-sensitive materials using these organic photoconductive materials have a low light-sensitivity and hence are yet insufficient as light-sensitive materials.

Also, a laminated layer type electrophotographic light-sensitive material separating the function into a charge generating layer and a charge transfer layer has been proposed but satisfactory light-sensitive materials of this type have not yet obtained.

That is, in a conventionally proposed laminated layer-type electrophotographic light-sensitive material having a charge generating layer and a charge transfer layer laminated, in succession, on a conductive support, the light-sensitivity is yet insufficient and there are problems that the light-sensitivity and the charged potential largely change with the change of environmental circumstances and the potential cycle deviation between an exposed portion and an unexposed portion is large.

Such a problem is also seen in an ordinary process of developing non-image portions on a photosensitive material with toner and transferring the toner images onto a transfer material such as paper, but the problem becomes remarkable in an image forming process including the steps of forming electrostatic latent images by uniformly negatively charging an electrophotographic light-sensitive material and imagewise exposing the light-sensitive material, forming toner images by toner development, and applying positive charges onto the light-sensitive material at the transfer of the toner images onto a transfer material such as paper. That is, since the potentials at the exposed portions and the non-exposed portions of the aforesaid light-sensitive material cause great cycle deviations, the density of the transferred images differs greatly between the initial image and images after copying many copies and fog is formed on the transferred images, as well as when after copying a large amount of copies, the size of transfer papers is changed to a larger size, there are problems that the transferred density at the widened portions of the large-sized transfer papers becomes high and fog is formed in these portions.

SUMMARY OF THE INVENTION

This invention has been made under the aforesaid circumstances and an object of this invention is to solve the above-described problems in conventional techniques.

That is, the object of this invention is to provide an electrophotographic light-sensitive material having a good charging property and a high light sensitivity, wherein the light sensitivity and charged potential are stable to environmental changes and also the potentials at the exposed portions and non-exposed portions are stable even in the case of copying many copies.

Another object of this invention is to provide an electrophotographic light-sensitive material which is suitably used for an image forming process including the steps of forming electrostatic latent images by uniformly negatively charging the electrophotographic light-sensitive material followed by imagewise exposure, forming toner images by attaching negatively charged toners to the low-potential portions (exposed portions) of the electrostatic latent images, and transferring the toner images by applying an electrostatic charge of a definite polarity.

A further object of this invention is to provide a process of forming electrophotographic images capable of giving images having a uniform image density without causing large cycle deviation of the potentials at the exposed portions and non-exposed portions when the aforesaid electrophotographic light-sensitive material is applied to the aforesaid electrophotographic process.

It has now been discovered that the aforesaid objects of this invention can be attained by an electrophotographic light-sensitive material comprising a conductive support having formed thereon, in succession, a charge generating layer and a charge transfer layer, wherein the charge generating layer comprises a binder resin containing therein a positive hole transferring charge generating pigment and a dicyanovinyl compound or coumarin compound represented by formula (I) shown below.

That is, according to the present invention, there is provided an electrophotographic light-sensitive material comprising a support having formed thereon, in succession, a charge generating layer and a charge transfer layer, wherein the charge generating layer comprises a binder resin containing therein a positive hole-transferring charge generating pigment and at least one compound represented by following formula (I);

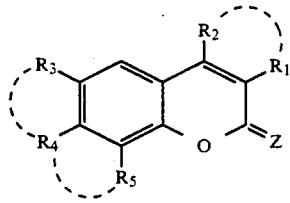

(I)

wherein Z represents

or an oxygen atom; $R_1$ represents a hydrogen atom, an alkyl group, —CN, —COOH, —COOR$_6$ (wherein $R_6$ represents an alkyl group), an aryl group,

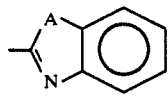

(wherein A represents an oxygen atom or a sulfur atom), or

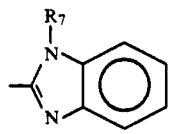

(wherein $R_7$ represents an alkyl group); $R_2$ represents a hydrogen atom, an alkyl group, or a halogenated alkyl group; $R_3$ represents a hydrogen atom or an alkyl group; $R_4$ represents a hydrogen atom, an alkyl group, —OH, —NH$_2$, —NHR$_8$ (wherein $R_8$ represents an alkyl group), or —NR$_9$R$_{10}$ (wherein $R_9$ and $R_{10}$ each represents an alkyl group); and $R_5$ represents a hydrogen atom or an alkyl group, said $R_1$ and $R_2$ may combine with each other to form a ring and two or three of said $R_3$, $R_4$, and $R_5$ may combine with each other to form a ring.

DETAILED DESCRIPTION OF THE INVENTION

Then, the electrophotographic light-sensitive material of this invention is described in detail.

FIG. 1 to 4 each is a schematic sectional view showing the laminated layer structure of each embodiment of the electrophotographic light-sensitive materials of this invention.

Figure 1:
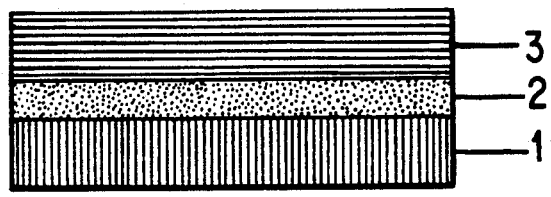
FIG. 1 to FIG. 4 each is a schematic sectional view showing the structure of each embodiment of the electrophotographic light-sensitive materials of this invention.

In the embodiment of this invention shown by FIG. 1, a charge generating layer 1 and a charge transfer layer 2 are formed, in succession, on a conductive support 1.

Figure 2:
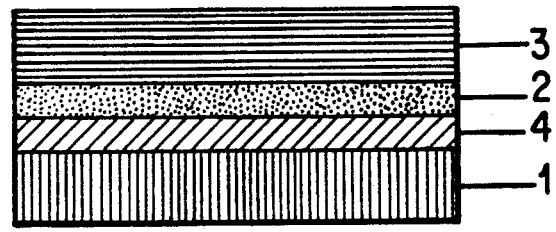

In the embodiment of this invention shown by FIG. 2, a subbing layer 4 is formed between a conductive support 1 and a charge generating layer 2, and a charge transfer layer 3 is formed on the charge generating layer 2.

Figure 3:
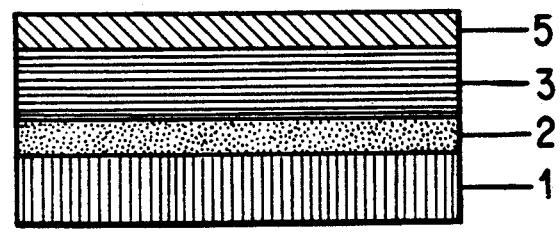

In the embodiment of this invention shown by FIG. 3, a charge generating layer 2 and a charge transfer layer 3 are formed on a conductive support 1 and a protective layer 5 is further formed on the surface of the charge transfer layer 3.

Figure 4:
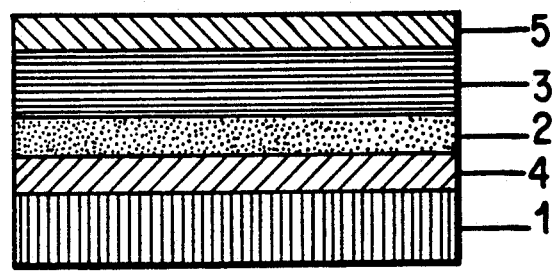

Also, in the embodiment of this invention shown by FIG. 4, a subbing layer 4 is formed between a conductive layer 1 and a charge generating layer 2, and also a protective layer 5 is formed on the surface of a charge transfer layer 3 formed on the charge generating layer 2.

Then, each layer constituting the electrophotographic light-sensitive material of this invention is explained in detail.

As the conductive support, there are a drum of a metal such as aluminum, copper iron, zinc, nickel, etc.; sheets, papers, plastics, and glass plates vapor-deposited by a metal such as aluminum, copper, gold, silver, platinum, pallasium, titanium, nickel-chromium, stainless steel, copper-indium, etc., or vapor-deposited by a conductive metal compound such as indium oxide, tin oxide, etc., or laminated with a metal foil; and drums, sheets, or plates subjected to a conductive treatment by coating a dispersion of carbon black, a indium oxide powder, a tin oxide-antimony oxide powder, a metal powder, etc., in a binder resin.

Furthermore, if necessary, the surface of the conductive support can be subjected to various treatments in the range of giving no influence on the image quality.

For example, an oxidation treatment, a chemical treatment, or a .coloring treatment may be applied to the surface thereof, or for preventing the occurrence of an interference fringe formed in the case of using a coherent light such as laser light for image exposure, a light-absorbing layer may be formed on the surface of the conductive support or a light-scattering treatment may be applied to the surface thereof.

As a method for the light-scattering treatment, a sand blast method, a liquid horning method, a pumice polishing method, a buff polishing method, a belt sander method, a brush polishing method, a steel wool polishing method, an acid etching method, an alkali etching method, an electrochemical etching method, etc., can be used.

Also, a subbing layer may be further formed between the conductive support and the charge generating layer.

The subbing layer shows a function of inhibiting the injection of electrostatic charges from the conductive support into the light-sensitive (photoconductive) layer at electrostatically charging the light-sensitive layer composed of the laminated layer structure and at the same time the function as an adhesive layer for adhereing and keeping the light-sensitive layer to the conductive support in a body, or, as the case may be, the function of preventing the light reflection at the conductive support.

As the binder resin being used for the subbing layer, there are polyethylene, polypropylene, an acrylic resin, a methacrylic resin, a polyamide resin, a vinyl chloride resin, a vinyl acetate resin, a phenol resin, polycarbonate, polyurethane, a polyimide resin, a vinylidene chloride resin, a polyvinyl acetal resin, a vinyl chloride-vinyl acetate copolymer, polyvinyl alcohol, a water-soluble polyester, nitrocellulose, casein, gelatin, etc.

Also, the thickness of the subbing layer is from 0.01 to 10 μm, and preferably from 0.05 to 3 μm. The subbing layer can be formed by a blade coating method, a Mayer bar coating method, a spray coating method, a dip coating method, a bead coating method, an air knife coating method, a curtain coating method, etc.

The charge generating layer constituting the light-sensitive layer on the conductive support in this invention is composed of a positive hole transferring charge generating pigment, the compound shown by the aforesaid formula (I), and a binder resin.

In formula (I), the alkyl group for $R_1$ to $R_{10}$ and the halogenated alkyl group for $R_2$ generally have 1 to 10 carbon atoms and preferably 1 to 5 carbon atoms. The alkyl group or the alkyl moiety of the halogenated alkyl group may be straight, branched or cyclic. The aryl group for $R_1$ is exemplified with a phenyl group and it may be substituted with a halogen atom. The $R_1$ and $R_2$ may combine to form a ring such as a cyclohexene ring and a benzene ring, which may be substituted with a halogen atom or an alkyl group. Further, two or three of the $R_3$, $R_4$ and $R_5$ may combine to form a ring which may be substituted with a halogen atom, an alkyl group, a cyano group, a carboxylic acid group or a carboxylate group, for example,

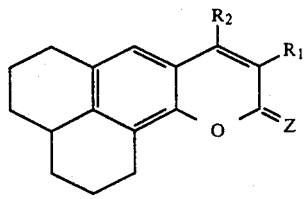

The charge generating pigment which is used together with the compound shown by formula (I) described above is required to have a positive hole-transferring property by itself. For finding whether or not a charge generating pigment has a positive hole-transferring property, a method of applying the pigment on abase material by vapor deposition or coating as a dispersion of the pigment in a resin at a high concentration, charging positively or negatively the layer of the pigment thus formed, and measuring the light decay. The term "positive hole-transferring charge generating pigment" in this invention means the pigment that the light decay at positive charging is large than the light decay at negative charging in the aforesaid method.

As the positive hole-transferring charge generating pigments for use in this invention, there are aquarylium series pigments, phthalocyanine series pigments, perylene series pigments, etc.

As the squarylium series pigments, there are the pigments represented by following formula (II):

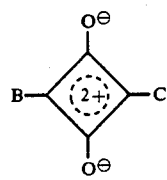

(II)

wherein B and C each represents a substituent (group) selected from those shown by following formulae;

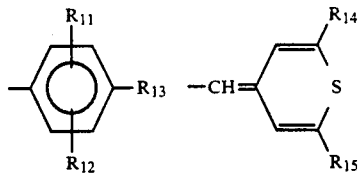

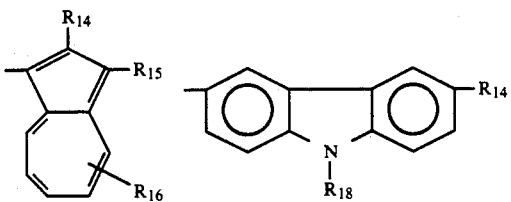

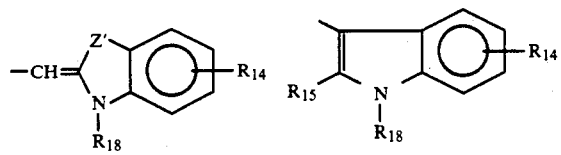

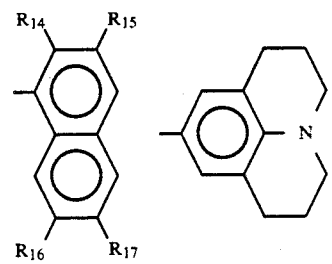

In the above formulae, $R_{11}$ and $R_{12}$ each represents a hydrogen atom, a hydroxy group, a fluorine atom, an alkyl group, $-NR_{19}R_{20}$ (wherein $R_{19}$ and $R_{12}$ each represents a hydrogen atom, a alkyl group, an aryl group, an alkylcarbonyl group, or an arylcarbonyl group), an alkoxy group, or an aryloxy group; $R_{13}$ represents $-NR_{21}R_{21}$ (wherein $R_{21}$ and $R_{22}$ each represents an alkyl group or an aryl group), $R_{14}$ to $R_{17}$ each represents a hydrogen atom, an alkyl group, an aryl group, $-CONHR_{23}$ (wherein $R_{23}$ represents an alkyl group or an aryl group), a halogen atom, an alkoxy group, or an aryloxy group, $R_{18}$ represents an alkyl group or an aryl group, and $Z'$ represents $CR_{24}R_{25}$, $-S-$, $-CR_{24}=CR_{25}-$ (wherein $R_{24}$ and $R_{25}$ each represents a hydrogen atom, an alkyl group, or an aryl group). The groups containing a carbon atom(s) for $R_{11}$ to $R_{25}$ generally have up to 10 carbon atoms and preferably up to 5 carbon atoms.

Practical examples of the aquarylium series pigment are illustrated below.

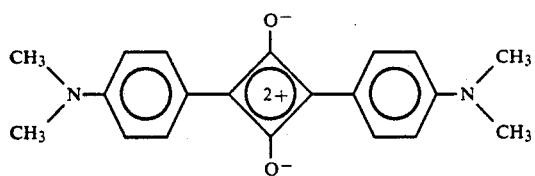
II-1
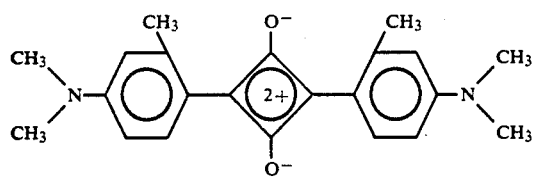
2
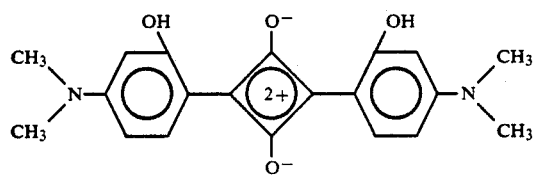
3
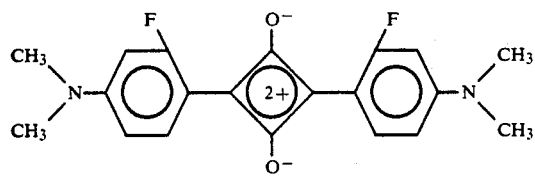
4
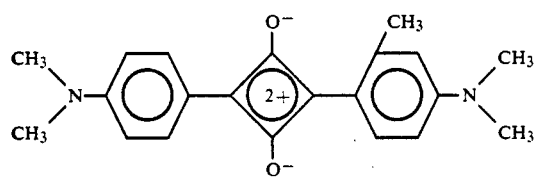
5
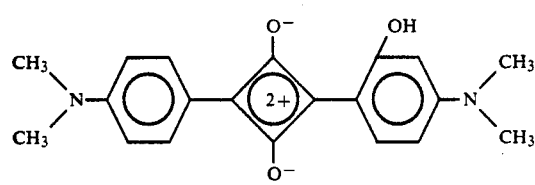
6
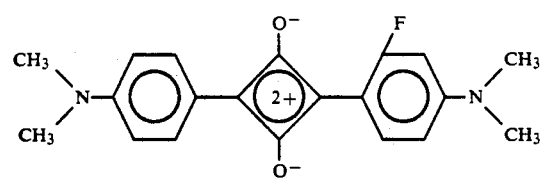
II-7
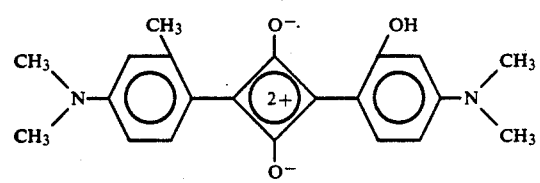
8
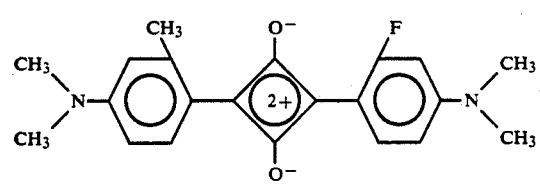
9

-continued
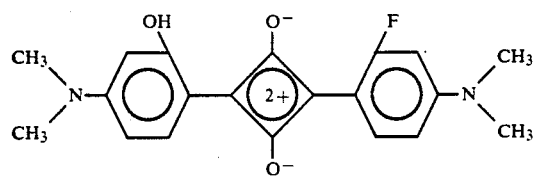
10
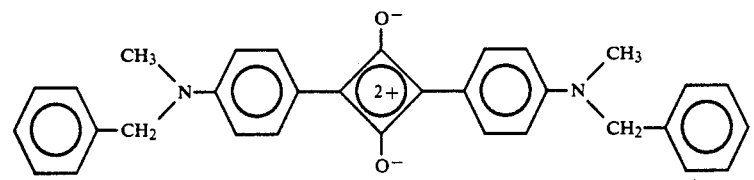
11
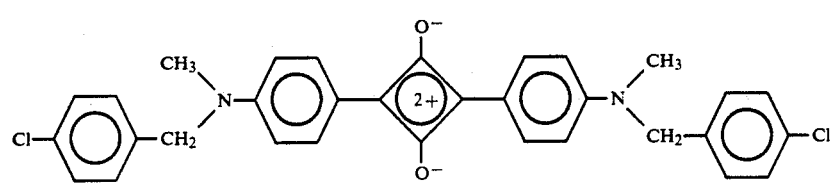
12
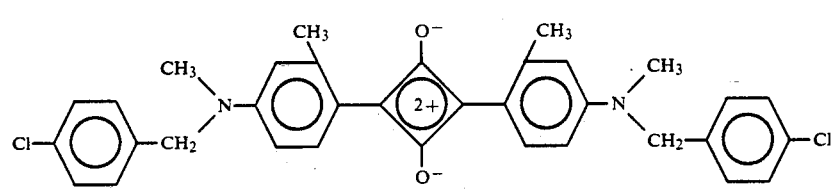
13
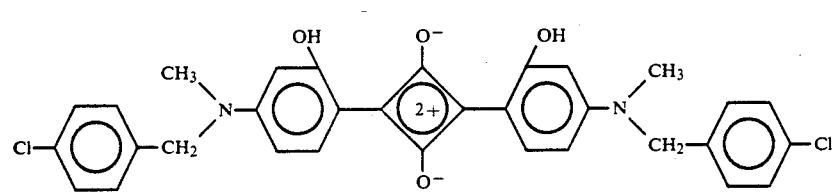
14
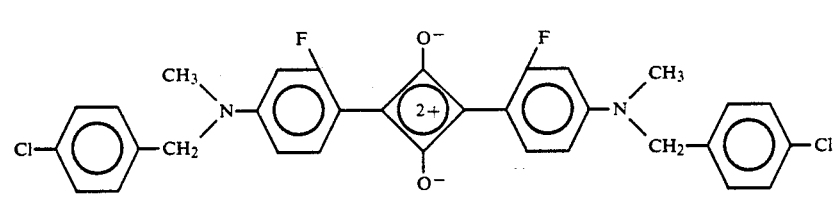
15
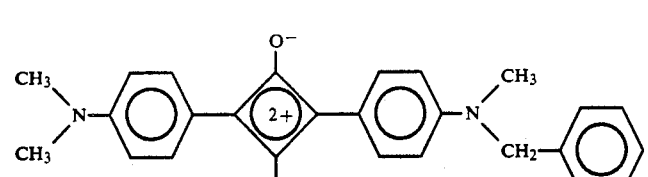
16
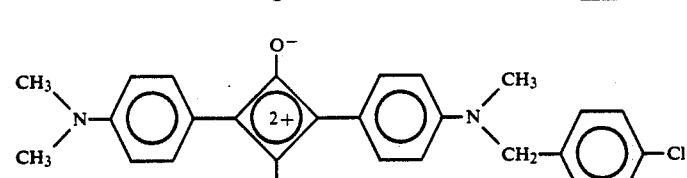
17
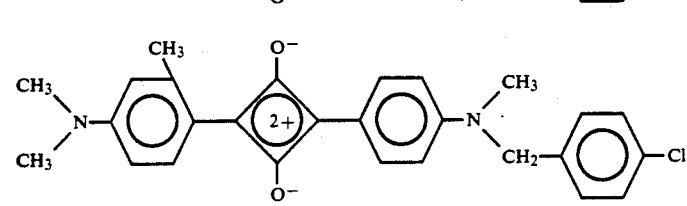
18

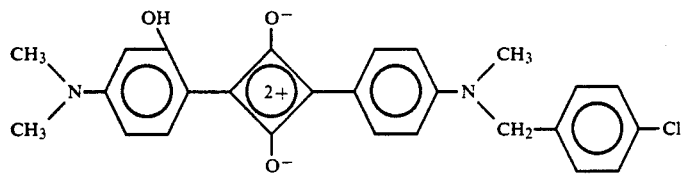
II-19
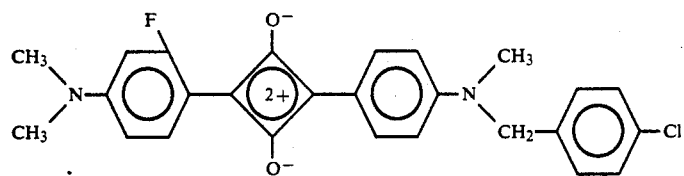
20
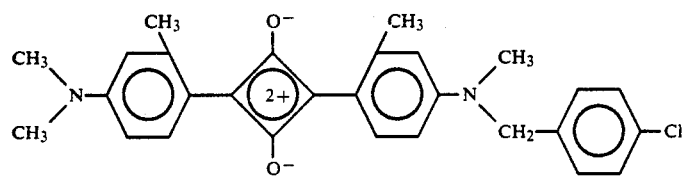
21
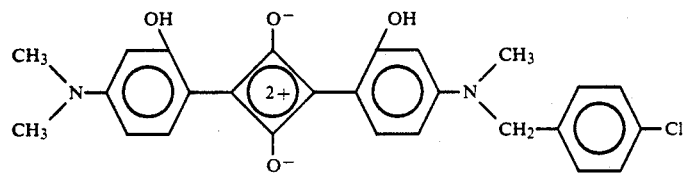
22
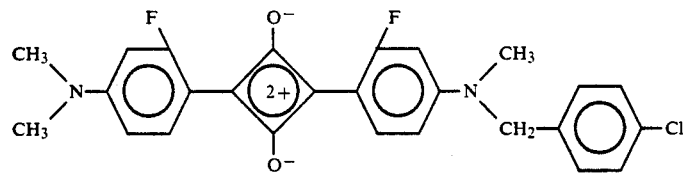
23
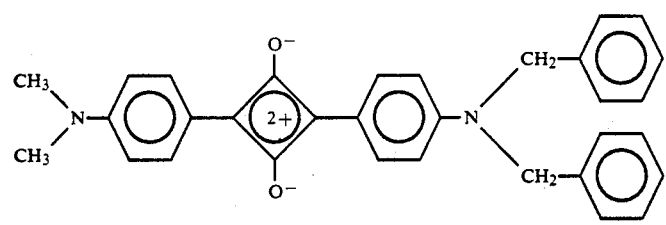
24
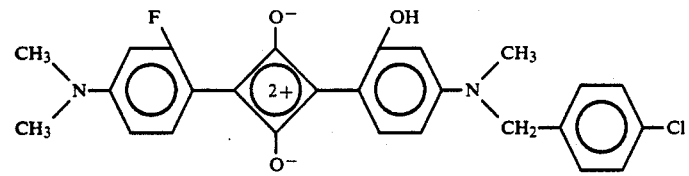
II-25
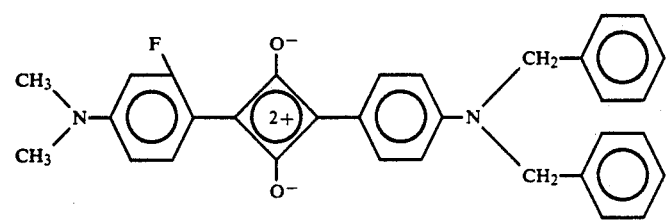
26

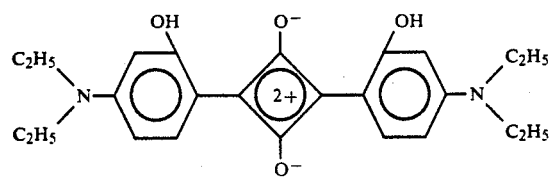
27
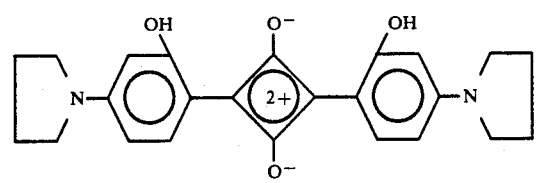
28
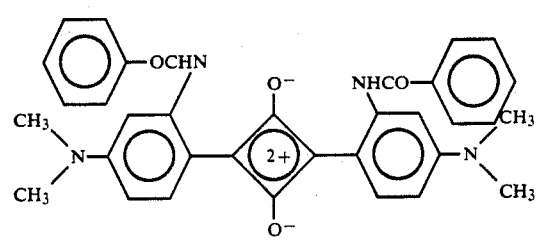
29
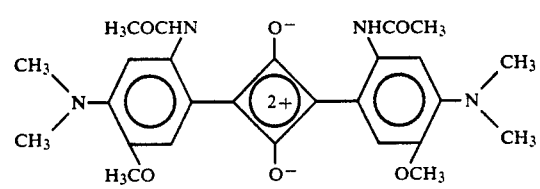
30
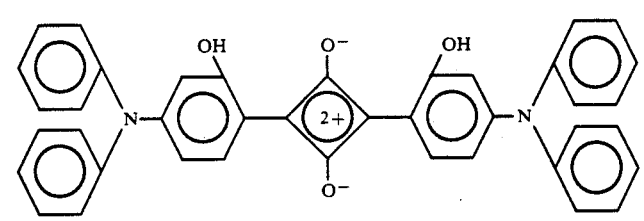
II-31
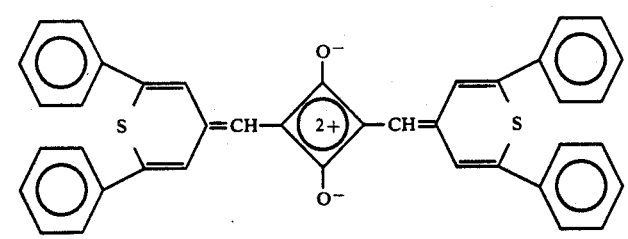
32
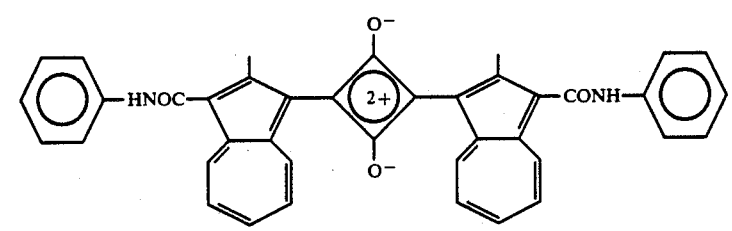
33

-continued
34
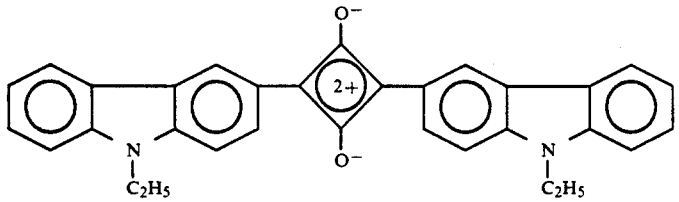
35
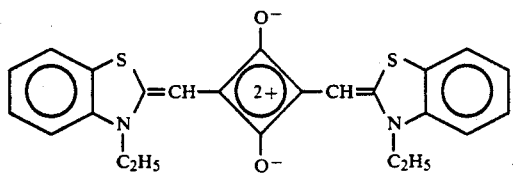
II-36
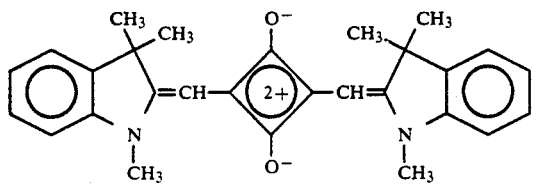
37
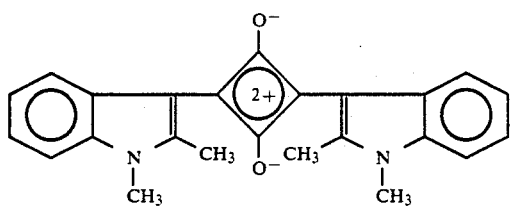
38
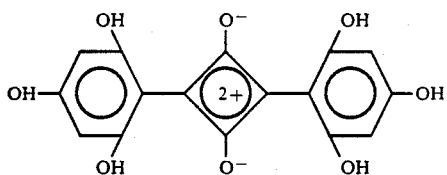
39
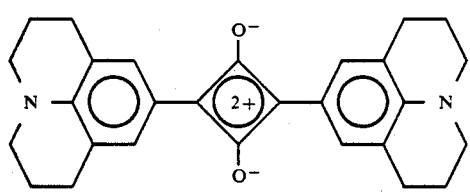
40
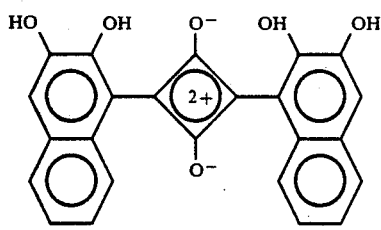
41
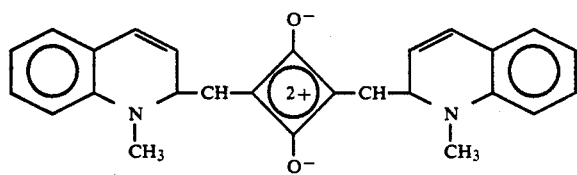
As the phthalocyanine series pigments, there are the pigments shown by following formula (III);

(III)

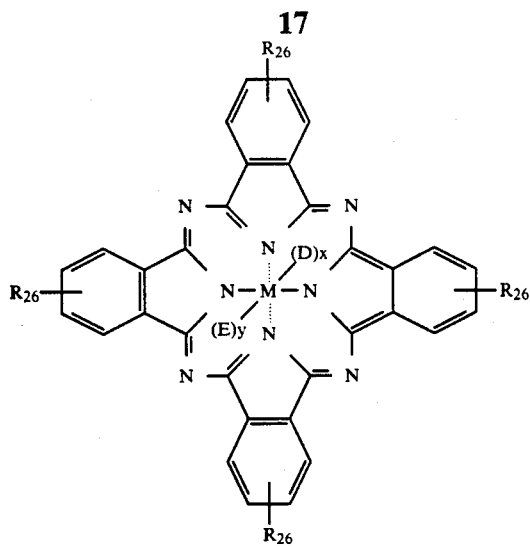

wherein R$_{26}$ represents a hydrogen atom, an alkyl group generally having 1 to 10 carbon atoms and preferably 1 to 5 carbon atoms, an aryl group (e.g., a phenyl group) which may be substituted, a halogen atom, a cyano group, or a nitro group; M represents two hydrogen atoms or a metal atom selected from Cu, Ni, Co, Fe, Mn, Cr, Tl, Ru, Pd, In, Sn, Sb, Zn, Mg, Ga, Ge, As, Si, Hg, Ti, V, U, Al and Pd; D and E each represents a halogen atom or an oxygen atom; and x and y each represents 0 or 1; however, when M is a divalent metal atom, x and y each is 0; when M is a trivalent atom, x is 1 and y is 0; when M is a tetravalent atom, x and y each is 1; When M is V, D is an oxygen atom, x is 1, and y is 0; and M is U, D and E each is an oxygen atom and x and y each is 1.

Practical examples of the phthalocyanine series pigment are non-metal phthalocyanine, copper phthalocyanine, vanazyl phthalocyanine, thitanyl phthalocyanine, aluminum phthalocyanine, gallium phthalocyanine, indium phthalocyanine, thallium phthalocyanine silicon phthalocyanine, germanium phthalocyanine, tin phthalocyanine, lead phthalocyanine, and the halides of the aforesaid phthalocyanines.

Also, as the perylene series pigments, there are the compounds shown by following formula (IV);

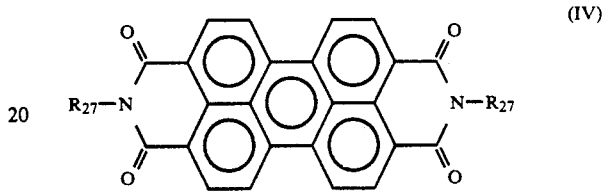

(IV)

wherein R$_{27}$ represents an alkyl group generally having 1 to 10 carbon atoms and preferably 1 to 5 carbon atoms or an aryl group (e.g., phenyl group), each may be substituted.

Practical examples of the perylene series pigment are illustrated below.

IV-1
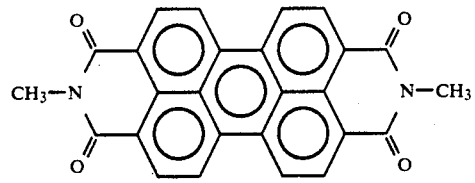

2
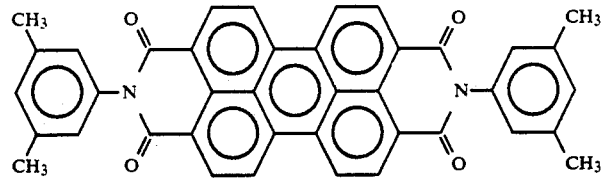

3
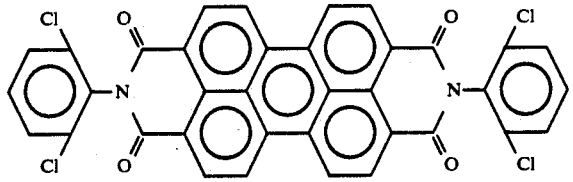

4
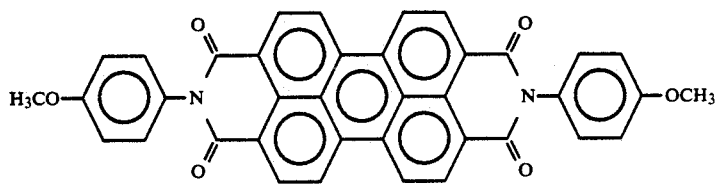

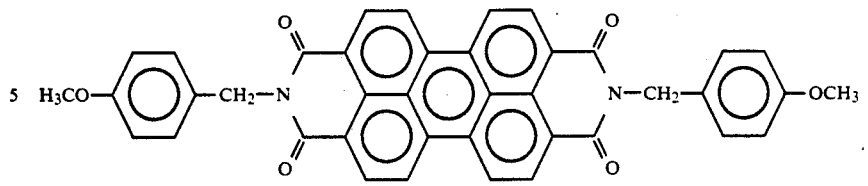
On the other hand, specific examples of the dicyanovinyl compound shown by aforesaid formula (I) wherein Z is
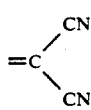
are as follows.
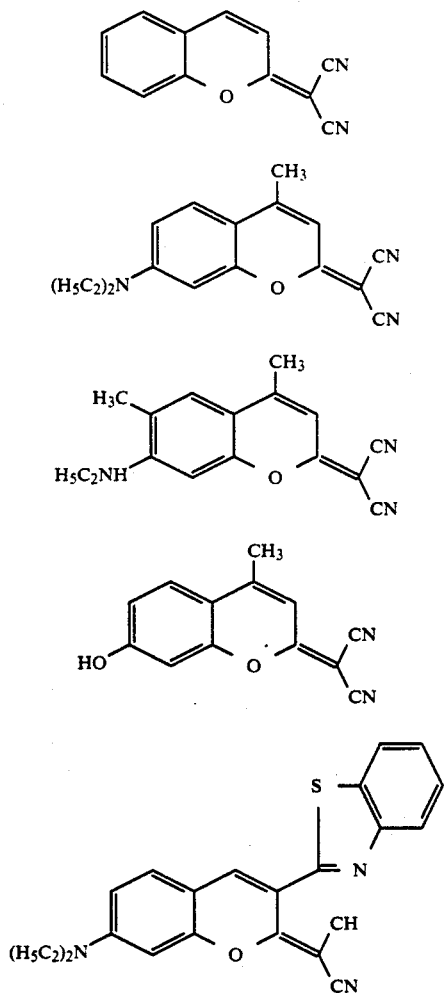
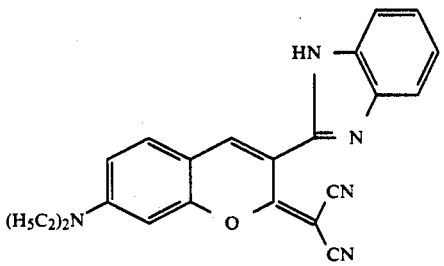

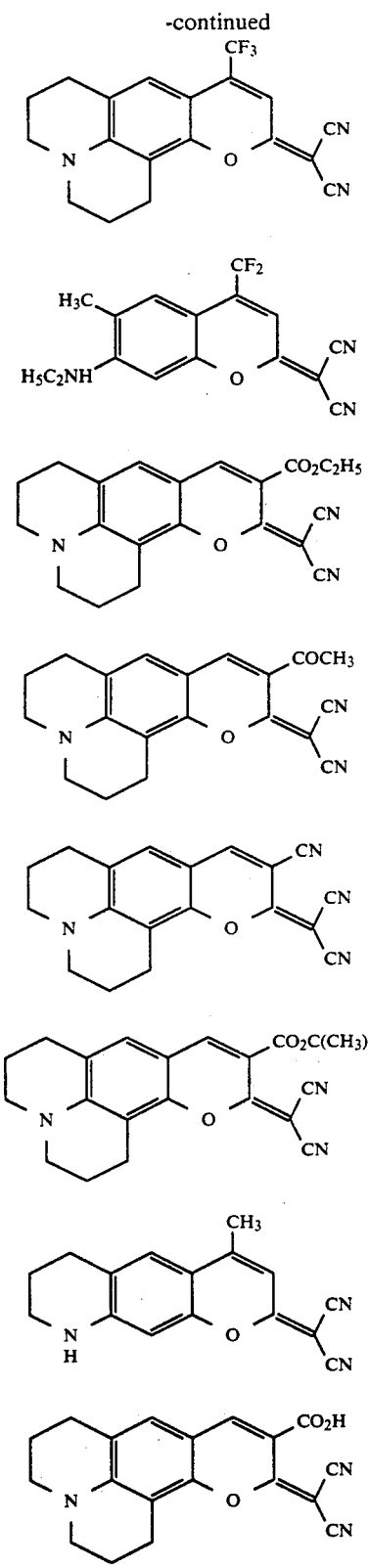
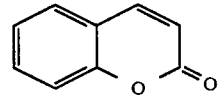
I'-1
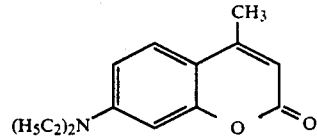
I'-2
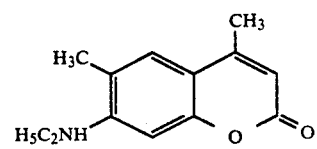
I'-3
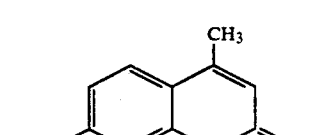
I'-4
I'-5
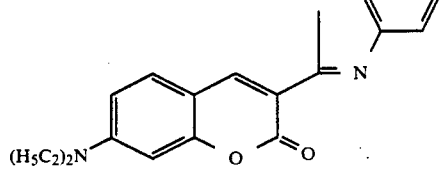
I'-6
I'-7
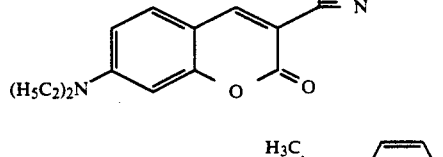
I'-8
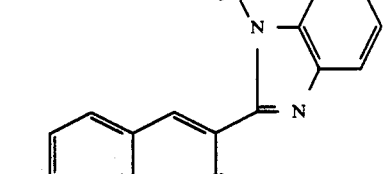
I'-9
Also, specific examples of the coumarin compound shown by aforesaid formula (I) wherein Z is an oxygen atom are as follows.

-continued

I'-9

[Structure I'-9: coumarin with CF2 and NH2 substituents]

I'-10

[Structure I'-10: coumarin with CF2 and (H3C)2N substituents]

I'-11

[Structure I'-11: julolidine-fused coumarin with CF3]

I'-12

[Structure I'-12: coumarin with CF2, H3C, and H5C2NH substituents]

I'-13

[Structure I'-13: julolidine-fused coumarin with CO2C2H5]

I'-14

[Structure I'-14: julolidine-fused coumarin with COCH3]

I'-15

[Structure I'-15: julolidine-fused coumarin with CN]

I'-16

[Structure I'-16: julolidine-fused coumarin with CO2C(CH3)2]

I'-17

[Structure I'-17: tetrahydroquinoline-fused coumarin with CH3]

I'-18

-continued

I'-19

[Structure I'-19: julolidine-fused coumarin with CO2H]

As a binder resin for the aforesaid positive hole-transferring charge generating pigment and the aforesaid compound shown by formula (I), there are polystyrene, a polycarbonate resin, an acrylic resin, a methacrylic resin, polyester, a vinylic resin, a silicone resin, cellulose derivatives, an alkyd resin, etc.

In the charge generating layer in this invention, the compound shown by formula (I) is contained in an amount of from 0.01 to 2 equivalents, and preferably from 0.1 to 1 equivalent to the positive hole-transferring charge generating pigment.

If the content of the compound shown by formula (I) is less than 0.01 equivalent, the aforesaid effects for increasing the light sensitivity and the reduction of the deviation of the potentials of the exposed portions and unexposed portions by the deviation of surrounding condition or by repeating use is reduced. If the content is large than 2 equivalents, the dark decay is greatly increased, the charged potential is reduced, and in an electrophotographic process of forming toner images at non-exposed portions, the background portions are liable to be fogged.

Also, it is preferred that the positive hole-transferring charge generating pigment is compounded with a binder resin in an amount of from 0.1 to 10 parts by weight, preferably 1 to 10 parts by weight to 1 part by weight of the binder resin.

For incorporating the aforesaid positive hole-transferring charge generating pigment and the compound shown by formula (I) in the coating composition for forming the charge generating layer, various methods can be employed.

In one of the methods, the positive hole-transferring charge generating pigment and the compound of formula (I) are dispersed in a solvent solution of a binder resin. In another method, the positive hole-transferring charge generating pigment is first dispersed in a solvent solution of a binder resin and then the compound of formula (I) is added to the dispersion. Also, in still another method, the positive hole-transferring charge generating pigment is previously treated with a solution of the compound of formula (I) to adsorb the compound onto the pigment and then dispersed in a solvent solution of a binder resin. Furthermore, in another method, the positive hole-transferring charge generating pigment is dispersed in a solvent solution of a binder resin, the dispersion is coated to form a film or layer, and then the film is treated with a solution of the compound of formula (I), thereby the film is impregnated with the compound.

For carrying out the aforesaid dispersion, an ordinary means such as a ball mill, a roll mill, an attritor, a sand mill, etc., can be used. At the dispersion, it is preferred that the mean particle size of the particles of the positive hole-transferring charge generating pigment is less than 3 μm, and particularly preferably less than 0.5 μm.

Also, as a solvent which is used at dispersing, any solvents capable solving the binder resin can be used, but it is preferred that the solvent having a good dispersibility for the pigment be selectively used. These solvents may be used singly or as a mixture thereof.

As a coating method for forming the charge generating layer, an ordinary method such as a blade coating method, a Mayer bar coating method, a spray coating method, a dip coating method, a bead coating method, an air knife coating method, a curtain coating method, etc., can be used.

The thickness of the charge generating layer is generally from 0.05 to 5 μm, and preferably from 0.1 to 2.0 μm.

The charge transfer layer of the electrophotographic light-sensitive material of this invention is composed of a charge transferring material contained or dispersed in a binder resin.

Examples of the charge transferring material are oxadiazole derivatives such as 2,5-bis(p-diethylaminophenyl)-1,3,5-oxadiazole, etc.; pyrazoline derivatives such as 1,3,5-triphenyl-pyrazoline, 1-[pyridyl-(2)]-3-(p-diethylaminostyryl)-5-(p-diethylaminophenyl)pyrazoline, etc.; aromatic tertiary amino compounds such as triphenylamine, dibenzylaniline, etc.; aromatic tertiary diamino compounds such as N,N'-bis(3-methylphenyl)-[1,1'-biphenyl]-4,4'-diamine, etc.; 1,2,4-triazine derivatives such as 3-(4'-dimethylaminophenyl)-5,6-di-(4'-methoxyphenyl)-1,2,4-triazine, etc.; hydrazone derivatives such as 4-diethylaminobenzaldehyde-1,1'-diphenylhydrazone, etc.; quinazoline derivatives such as 2-phenyl-4-styrylquinazoline, etc.; benzofurane derivatives such as 6-hydroxy-2,3-di-(p-methoxyphenyl)-benzofurane, etc.; α-stilbene derivatives such as p-(2,2-diphenylvinyl)-N,N-diphenylaniline, etc.; the anamine derivatives described in *Journal of Imaging Science*, 29, 7-10(1985); carbazole derivatives such as N-ethylcarbazole, etc.; poly-N-vinylcarbazole and derivatives thereof; poly-γ-carbazolylethyl glutamate and derivatives thereof; pyrene, polyvinylpyrene, polyvinylanthracene, polyvinylacridine, poly-9-biphenylanthracene, pyrene-formaldehyde resins, and ethyl carbazole-formaldehyde resins.

Also, these charge transferring materials can be used singly or as a mixture thereof.

Furthermore, as the binder resin for use in this invention, there are a polycarbonate resin, a polyester resin, a polyacrylate resin, a methacrylic resin, an acrylic resin, a vinyl chloride resin, a vinylidene chloride resin, a polystyrene resin, a polyvinyl acetal resin, a styrene-butadiene copolymer, a vinylidene chloride-acrylonitrile copolymer, a vinyl chloride-vinyl acetate copolymer, a vinyl chloride-vinyl acetate-maleic anhydride copolymer, a silicone resin, a silicone-alkyd resin, a phenol-formaldehyde resin, a styrene-alkyd resin, a poly-N-vinylcarbazole, etc. These binder resins can be used singly or as a mixture thereof.

The compounding ratio of the charge transferring material/binder resin is preferably from 10/1 to 1/5 by weight ratio. The thickness of the charge transfer layer in this invention is generally from 5 to 50 μm, and preferably from 10 to 30 μm.

As a coating method for forming the charge transfer layer, a blade coating method, a Mayer bar coating method, a spray coating method, a dip coating method, a bead coating method, a curtain coating method, etc., can be used.

Furthermore, as the solvent which is used for forming the charge transfer layer, there are aromatic hydrocarbons such as benzene, toluene, xylene, chlorobenzene, etc.; ketones such as acetone, 2-butanone, etc.; halogenated aliphatic hydrocarbons such as methylene chloride, chloroform, ethylene chloride, etc.; and cyclic or straight chain ethers such as tetrahydrofuran, ethyl ether, etc. These organic solvents can be used singly or as a mixture.

In the electrophotographic light-sensitive material of this invention, if necessary, a protective layer may be formed on the charge transfer layer.

The protective layer is used for preventing the occurrence of the chemical denature of the charge transfer layer at charging the light-sensitive layer composed of the laminated layer structure and at the same time for improving the mechanical strength of the light-sensitive layer.

The protective layer is formed by coating a coating composition composed of a suitable binder resin containing an electrically conductive material.

As the conductive material, there are metallocene compounds such as N,N'-dimethylphellocene, etc.; aromatic amino compounds such as N,N'-diphenyl-N,N'-bis(3-methylphenyl)-[1,1'-phenyl]-4,4'-diamine, etc.; and metal oxides such as antimony oxide, tin oxide, titanium oxide, indium oxide, tin oxide-antimony oxide, etc.

As the binder resin for the protective layer, there are a polyamide resin, a polyurethane resin, a polyester resin, an epoxy resin, a polyketone resin, a polycarbonate resin, a polyvinyl ketone resin, a polystyrene resin, a polyacrylamide resins, etc.

The thickness of the protective layer is from 0.5 to 20 μm, and preferably from 1 to 10 μm.

The electrophotographic light-sensitive material of this invention can be used for a known electrophotographic image-forming process. That is, the electrophotographic light-sensitive material can be used for an image-forming process including the steps of uniformly charging the surface of the light-sensitive layer, imagewise exposing the charged surface to form electrostatic latent images, and developing the electrostatic latent images with charged toner particles, and copy images of stabilized image density can be always obtained.

However, the electrophotographic light-sensitive material of this invention is particularly suitable for use in an image-forming process of forming images by a so-called reversal developing process.

That is, the electrophotographic light-sensitive material is particularly suitable for an image-forming process comprising the steps of uniformly negatively charging the surface of the electrophotographic light-sensitive material, imagewise exposing the surface to form electrostatic latent images, attaching negatively charged toner particles to the low potential portions (exposed portions) of the electrostatic latent images to form toner images, superimposing a transfer material on the electrophotographic light-sensitive material having the toner images thus formed, applying positive charges from the back side of the transfer material, and, thus, transferring the toner images onto the transfer material.

Then, the image-forming process to which the electrophotographic light-sensitive material of this invention is applied is explained.

For uniformly charging the surface of the electrophotographic light-sensitive material, a corona discharging device such as corotron, scorotron, dicorotron, pincorotron, etc., or a charging roller, etc., can be used. It is preferred that the initial charging potential be selected in the range of from −700 V to −200 V.

As the image exposure means, an illuminating optical system composed of an illumination lamp and an image focusing optical system, a laser exposure optical system composed of a laser light generating source and a laser light polarizer, a LED (light emitting diode) array, a liquid crystal light bulb, a vacuum fluorescent tube array, an optical fiber array, a light wave guide array, etc., can be used, but it is preferred to use a light source emitting light having a wavelength in the spectral sensitizing wavelength region of the electrophotographic light-sensitive material to be used.

Electrostatic latent images formed by the imagewise exposure is developed using a developer to form toner images. As the developer, a two-component developer composed of a carrier and a toner or a one-component developer composed of a toner only can be used. The toner particles may be magnetic toner particles containing a magnetic powder in the inside thereof or non-magnetic toner particles.

At development, toner particles are brought into close to or contact with the electrostatic latent images using a developing apparatus having a means for retaining the developer, whereby the toner particles are selectively attached to the latent images according to the potential.

In this case, according to the charged polarity of the toner, the toner attaches to the low potential portions (exposed portions) of the electrostatic latent images on the light-sensitive material (reversal development) or attaches to the high potential portions (non-exposed portions) thereof (normal development) and the system can be practiced by selecting the charged polarity of toner.

Since the electrophotographic light-sensitive material of this invention has essentially a negative-charging property, in the reversal development, a toner having a negative-charging property is selected and in the case of normal development, a toner having a positive-charging property is selected.

At development, a bias voltage is applied between the support of the electrophotographic light-sensitive material and the developer-retaining means. As the bias voltage, a direct current voltage or an alternating current voltage formed by overlapping direct current voltages can be used.

In particular, in the case of carrying out the reversal development, it is necessary to apply a bias voltage same as or lower than the potential of unexposed portions.

The toner images formed by the development can be transferred onto a transfer material by an optional method. As the transferring means, the aforesaid corona charging device as well as transfer roll, a press roll, etc., applied with a transferring potential can be used. But, in particular, an electric field transferring method in which the transfer is carried out by applying electrostatic charges from the back surface of the transfer material using a corona discharging device is effective. For example, in the case of the images of negatively charged toner particles formed by a reversal development, the toner images is suitably transferred onto a transfer material by applying positive corona discharging from the back surface of the transfer material.

After finishing the image transfer, if necessary, remaining toner images (i.e., toner images which were not transferred) on the electrophotographic light-sensitive material are cleaned and electrostatic charges on the light-sensitive material are eliminated by an optional light charge-eliminator or corona charge-eliminator for the subsequent image-forming step.

Also, the electrophotographic light-sensitive material can be suitably used for a so-called one pass multicolor image-forming process.

For example, the light-sensitive material can be suitably used for an image-forming process wherein after uniformly negatively charging the surface of the electrophotographic light-sensitive material, a 1st imagewise exposure is applied thereto to form a 1st electrostatic latent image, a negatively charged toner is attached to the low-potential portions of the 1st electrostatic latent image to form a 1st toner image; then a 2nd imagewise exposure is applied thereto to form a 2nd electrostatic latent image and a positively charged toner is attached to the higher-potential portions of the 2nd electrostatic latent image to form a 2nd toner image; then, after making the polarities of the 1st and 2nd toner images equal to one of the polarities, a transfer material is superposed on the electrophotographic light-sensitive material retaining the 1st and 2nd toner images, electrostatic charges of the opposite polarity to that of the 1st and 2nd toner images are applied from the back surface of the transfer material, and, thus, the 1st and 2nd toner images are transferred onto the transfer material.

In the aforesaid 1 pass multicolor image-forming process, as the means for uniformly negatively charging the electrophotographic light-sensitive material, the image-exposure means, the developing means, and image-transferring means, the means described above can be used.

First, the surface of the electrophotographic light-sensitive material is uniformly negatively charged and then the 1st imagewise exposure is applied thereto. For the 1st imagewise exposure, an imaged portion exposure for exposing the portions corresponding to the imaged portions is employed. The 1st electrostatic latent image thus formed is developed using a 1st developer to form a 1st toner image. In this case, a negatively charged 1st toner is attached to the low potential portions (exposed portions) of the 1st electrostatic latent image using a developer retainer to which a bias voltage lower than the initially charged potential to form a 1st toner image.

Then, a 2nd imagewise exposure is applied and in the 2nd imagewise exposure, a background exposure for exposing the portions corresponding to the background portions is employed. Also, it is preferred that as the light source for the 2nd image exposure, a light source the intensity of which is weaker than that of the light source for the 1st image exposure, which exposes in such a manner that the potential of the portions of the light-sensitive material corresponding to the background portions is reduced to almost a half of the initially charged potential.

Then, a positively charged 2nd toner is attached to the portions which were not exposed in the 2nd imagewise exposure (i.e., the imaged portions in the 2nd imagewise exposure). In this case, it is preferred to carry out the development by retaining the 2nd toner on a developer retaining means to which a bias voltage higher than the potential of the portions of the light-sensitive material corresponding to the background portions described above.

Also, since the 2nd developer is a so-called overlap development of applying onto the light-sensitive material already having thereon the 1st toner image, it is preferred to use a two-component developer composed of a toner and a low-density carrier having a negatively charging property at the 2nd development for preventing the occurrence of image disturbance of the 1st toner image and the intermixing of the 1st toner into the developing means for the 2nd toner. Also, it is preferred that the density of the carrier is not higher than 4.0 g/cm$^3$.

After forming the 1st and 2nd toner images on the electrophotographic light-sensitive material, these toner images are transferred onto a transfer material. In this case, since these toners have been charged to the opposite polarities to each other, it is necessary to make the polarities of the toners equal to one of the polarities. For making the polarities equal, corona discharging by a charging device may be applied before transferring the toner images. In this case, since the electrophotographic light-sensitive material of this invention has a negatively charging property, it is preferred to make the polarities of the toners equal to positive polarity. For charging before the transfer, an alternating current voltage formed by overlapping positive direct current voltages is preferably used.

Then, a transfer material is superposed on the toner images formed on the electrophotographic light-sensitive material and a charging potential of the opposite polarity of the toner images, for example, a charging potential of negative polarity in the case when the polarities of the toner images are made equal to positive polarity is applied thereto from the back surface of the transfer material, whereby the toner images are transferred onto the transfer material. In this case, it is preferred to a negative direct current voltage as the transferring potential.

The image transfer is performed as described above and in this case, as the 1st toner and the 2nd toner, the toners each having a proper color can be used. For example, when the electrophotographic light-sensitive material is a drum form, two-color images can be obtained in one rotation of the drum.

Then, the electrophotographic light-sensitive material of this invention and the image-forming process using the light-sensitive material are explained practically by the following examples.

EXAMPLE 1

The surface of an aluminum pipe having an outside diameter of 40 mm and a length of 319 mm, which was subjected to a mirror plane polishing treatment, was treated by liquid horning in such a manner that the surface roughness (Ra) became 0.18 μm. Then, a coating composition having the following components for forming a subbing layer was prepared.

| | |
|---|---|
| Polyamide Resin (Lackamide 5003, trade name, made by Dainippon Ink and Chemicals, Inc.) | 1 part by weight |
| Methanol | 5 parts by weight |
| n-Butanol | 3 parts by weight |
| Water | 1 part by weight |

The aforesaid coating composition was coated on the surface of the aluminum pipe by dip coating and dried for 10 minutes at 115° C. to form a subbing layer having a thickness of 1 μm.

Then, a mixture of the following components was prepared.

| | |
|---|---|
| X-type Non-metal Phthalocyanine | 1 part by weight |
| Polyvinyl Butyral Resin (Eslex BM1, trade name, made by Sekisui Chemical Co., Ltd.) | 1 part by weight |
| Dicyanovinyl Compound (Compound 1-5) | 0.3 equivalent to the pigment |
| Cyclohexanone | 60 parts by weight |

The aforesaid mixture was dispersed for 6 hours in a sand mill using glass beads of 1 mm in diameter to provide a dispersion of the pigment having a mean particle size of about 0.05 μm.

The dispersion was coated on the aforesaid subbing layer by a dip coating method and dried for 10 minutes at 100° C. to form a charge generating layer having a thickness of 0.2 μm.

Furthermore, a mixture of the following components was prepared.

| | |
|---|---|
| N,N'-Diphenyl-N,N'-bis(3-methyl-phenyl)-[1,1'-bisphenyl]-4,4'-diamine (having the following structure) | 2 parts by weight |

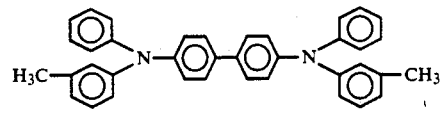

| | |
|---|---|
| Polycarbonate Resin (bisphenol Z type) | 3 parts by weight |
| Monochlorobenzene | 20 parts by weight |

The aforesaid mixture was coated on the charge generating layer thus formed by a dip coating method and dried for 60 minutes at 115° C. to form a charge transfer layer having a thickness of 20 μm.

The electrophotographic light-sensitive material thus prepared was negatively charged using a Scorotron (grid applied voltage: 340 V), exposed, then, to a semiconductor laser (780 nm oscillation) to cause light decay, and a probe of a surface electrometer was placed at a position of after 0.3 second (corresponding to the position of after 0.6 second since the charging), and the potential (VH) at non-exposure and the potential (VL: 30 erg/cm$^2$ exposure) after exposure were measured.

Furthermore, a Corotron (wire applied potential: +5.0 Kv) was placed behind the Scorotron, positively charged the light-sensitive material, and thereafter, the charges on the light-sensitive material was eliminated by a tungsten lamp.

In this system, the cycle of negative charging-light exposure-positive charging-charge eliminating exposure was defined one cycle and the changes of VH and VL until 100 cycles were measured. The results are shown in Table 1.

Also, the aforesaid electrophotographic light-sensitive material was mounted on a laser printer (XP-11, trade name, manufactured by Fuji Xerox Co.). The laser printer was for transferring toner images attached to the exposed portions of the electrophotographic light-sensitive material by a transferring Corotron of DC +4.8 Kv using a magnetic one-component toner of negatic polarity. After continuously printing 500 prints by the laser printer using A4 size (210 mm ×297 mm) papers, printing was further continued using B4 size (257 mm ×364 mm) papers only and the density difference of printout between the A4 size paper passed portion of the light-sensitive material and other portions (A4 paper non-passed portions) of the light-sensitive material was evaluated.

The result obtained is shown in Table 1 below.

EXAMPLES 2 TO 7

By following the same procedure as Example 1 except that the addition amount of the dicyanovinyl compound (Compound I-5) to the pigment was changed as shown in Table 1 below, each of electrophotographic light-sensitive materials was prepared and the density difference was evaluated on each sample as in Example 1.

The results obtained are shown in Table 1 below.

EXAMPLES 8 TO 10

By following the same procedure as Example 1 except that each of the dicyanovinyl compounds shown in Table 1 below was used in place of the dicyanovinyl compound, each of electrophotographic light-sensitive materials was prepared and the density difference was evaluated on each sample by the same manner as in Example 1.

The results obtained are shown in Table 1 below.

COMPARISON EXAMPLE 1

By following the same procedure as Example 1 except that the dicyanovinyl compound was not added, an electrophotographic light-sensitive material was prepared and the density difference was evaluated by the same manner as in Example 1.

The result obtained is shown in Table 1 below.

TABLE 1

| | Dicyanovinyl Compound | | Potential | 1 Cycle (V) | 100 Cycles (V) | Density difference of prints between A4 paper passed portion and non-passed portions after printing 500 prints |
| --- | --- | --- | --- | --- | --- | --- |
| | No. | Amount (equivalent) | | | | |
| Example 1 | I-5 | 0.3 | VH | −304 | −304 | No difference |
| | | | VL | −75 | −74 | " |
| Example 2 | I-5 | 0.01 | VH | −310 | −300 | " |
| | | | VL | −88 | −79 | " |
| Example 3 | I-5 | 0.1 | VH | −308 | −305 | " |
| | | | VL | −80 | −76 | " |
| Example 4 | I-5 | 0.2 | VH | −307 | −305 | " |
| | | | VL | −79 | −76 | " |
| Exmaple 5 | I-5 | 1.0 | VH | −300 | −298 | " |
| | | | VL | −70 | −69 | " |
| Exmaple 6 | I-5 | 2.0 | VH | −296 | −295 | " |
| | | | VL | −66 | −64 | " |
| Example 7 | I-5 | 4.0 | VH | −280 | −278 | " |
| | | | VL | −49 | −47 | " |
| Example 8 | I-1 | 0.3 | VH | −308 | −305 | " |
| | | | VL | −80 | −78 | " |
| Example 9 | I-9 | 0.3 | VH | −300 | −293 | " |
| | | | VL | −67 | −64 | " |
| Example 10 | I-17 | 0.3 | VH | −310 | −305 | " |
| | | | VL | −80 | −76 | " |
| Comparison Example 1 | — | — | VH | −310 | −278 | The density is higher at the A4 paper non-passed portions than the passed portion |
| | | | VL | −89 | −58 | |

A4 size: 210 mm × 297 mm

EXAMPLES 11 TO 15

By following the same procedure as Example 1 except that the compounds shown in Table 2 were used in place of x-type non-metal phthalocyanine and the dicyanovinyl compound in Example 1, each of electrophotographic light-sensitive materials was prepared and the density difference was evaluated by the same manner as in Example 1.

The results obtained are shown in Table 2 below.

COMPARISON EXAMPLES 2 TO 6

By following the same procedures as Example 11 to 15 except that dicyanovinyl compounds were not added, each of electrophotographic light-sensitive materials was prepared and the density difference was evaluated by the same manner as in Example 1.

The results obtained are shown in Table 2 below.

TABLE 2

| | Pigment No. | Dicyanovinyl Compound | Potential | 1 Cycle (V) | 100 Cycles (V) | Density difference of prints between A4 paper passed portion and non-passed portions after printing 500 prints |
| --- | --- | --- | --- | --- | --- | --- |
| Example 11 | ε-Type Copper Phthalocyanine | I-5 | VH | −303 | −300 | No difference |
| | | | VL | −69 | −64 | " |
| Example 12 | II-2 | I-11 | VH | −300 | −295 | " |
| | | | VL | −63 | −62 | " |
| Example 13 | II-4 | I-5 | VH | −308 | −306 | " |
| | | | VL | −80 | −78 | " |
| Example 14 | II-10 | I-2 | VH | −305 | −304 | " |
| | | | VL | −77 | −76 | " |
| Example 15 | II-17 | I-13 | VH | −300 | −299 | " |
| | | | VL | −72 | −69 | " |

TABLE 2-continued

|  | Pigment No. | Dicyanovinyl Compound | Potential | 1 Cycle (V) | 100 Cycles (V) | Density difference of prints between A4 paper passed portion and non-passed portions after printing 500 prints |
| --- | --- | --- | --- | --- | --- | --- |
| Comparison Example 2 | ε-Type Copper Phthalocyanine | — | VH<br>VL | −304<br>−75 | −271<br>−49 | The density of higher at the A4 paper non-passed portions than the passed portion |
| Comparison Example 3 | II-2 | — | VH<br>VL | −303<br>−79 | −265<br>−48 | The density of higher at the A4 paper non-passed portions than the passed portion |
| Comparison Example 4 | II-4 | — | VH<br>VL | −318<br>−95 | −290<br>−70 | The density of higher at the A4 paper non-passed portions than the passed portion |
| Comparison Example 5 | II-10 | — | VH<br>VL | −310<br>−97 | −288<br>−77 | The density of higher at the A4 paper non-passed portions than the passed portion |
| Comparison Example 6 | II-17 | — | VH<br>VL | −306<br>−85 | −280<br>−80 | The density of higher at the A4 paper non-passed portions than the passed portion |

EXAMPLES 16 TO 20

By following the same procedure as Example 1 except that a perylene pigment (Compound IV-1) was used as the charge generating pigment and each of the compounds shown in Table 3 below was used in place of the dicyanovinyl compound, each of electrophotographic light-sensitive materials was prepared. Then, the density difference was evaluated on each of the photographic light-sensitive materials thus prepared as in Example 1 except that a halogen lamp (filtered by an interference filter having a central wavelength of 550 nm) was used as the light source. The exposure amount was 20 erg/cm².

The results obtained are shown in Table 3 below.

COMPARISON EXAMPLE 7

By following the same procedure as Example 16 except that the dicyanovinyl compound was not added, an electrophotographic light-sensitive material was prepared and the density difference was evaluated by the same manner as in Example 16.

The results obtained are shown in Table 3 below.

TABLE 3

| | Pigment No. | Dicyanovinyl Compound | Potential | 1 Cycle (v) | 100 Cycles (V) |
| --- | --- | --- | --- | --- | --- |
| Example 16 | IV-1 | I-3 | VH<br>VL | −326<br>−118 | −321<br>−117 |
| Example 17 | IV-1 | I-5 | VH<br>VL | −325<br>−120 | −322<br>−116 |
| Example 18 | IV-1 | I-7 | VH<br>VL | −330<br>−130 | −328<br>−125 |
| Example 19 | IV-1 | I-11 | VH<br>VL | −320<br>−126 | −318<br>−119 |
| Example 20 | IV-1 | I-13 | VH<br>VL | −322<br>−131 | −318<br>−127 |
| Comparison Example 7 | IV-1 | — | VH<br>VL | −331<br>−160 | −300<br>−132 |

EXAMPLE 21 AND COMPARISON EXAMPLE 8

By following the same procedures as Example 1 and Comparison Example 1 except that an aluminum pipe having an outside diameter of 84 mm and a length of 340 mm, the surface of which has been subjected to a mirror plane polishing treatment, was used as the base material, electrophotographic light-sensitive materials were prepared.

Each of the electrophotographic light-sensitive materials thus prepared was mounted on a two-color laser printer (repeating the steps of charging, 1st laser exposure, negatively charged red toner development of the exposed portions, 2nd laser exposure, positively charged black toner development of the unexposed portions, charging by AC voltage formed by overlapping positive DC voltages before transferring, transferring the toner images by the application of negative DC charges by Corotron, cleaning, and charge elimination) prepared by modifying a copying apparatus, FX 5030 (trade name manufactured by Fuji Xerox Co.) and 500 prints each having a pattern of a mixture of red and black images were printed using B4 size papers. Then, the change of the densities of printout at the red portion and the black portion was observed.

The results showed that in the electrophotographic light-sensitive material of Example 21, clear outputs having no background fog on both the red portion and black portion were obtained, while in the electrophotographic light-sensitive material of Comparison Example 8, the formation of fog of red toner began to increase at the background portions with the increase of the continuously printed prints, the line of the red printouts began to thicker, and the density of the black outputs was lowered.

EXAMPLE 22

By following the same procedure as Example 1 except that a coumarin compound (Compound I'-1) was used in an amount of 0.2 equivalent to the amount of pigment in place of the dicyanovinyl compound, an electrophotographic light-sensitive material was prepared and the density difference was evaluated by the same manner as in Example 1.

The result obtained is shown in Table 4 below together with the result of Comparison Example 1.

EXAMPLES 23 TO 27

By following the same procedure as Example 22 except that the addition amount of the coumarin compound (Compound I'-1) to the pigment was changed as shown in Table 4 below, each of the electrophotographic light-sensitive materials was prepared and the density difference was evaluated on each same by the same manner as Example 1.

The results obtained are shown in Table 4.

EXAMPLES 28 TO 30

By following the same procedure as Example 22 except that each of the compound shown in Table 4 was used in place of the coumarin compound each of electrophotographic light-sensitive materials was prepared and the density difference was evaluated on each sample by the same manner as in Example 1.

The results obtained are shown in Table 4.

were used on place of x-type non-metal phthalocyanine and the coumarin compound, each of electrophotographic light-sensitive materials was prepared and the density difference was evaluated on each sample by the same manner as in Example 1.

The results obtained are shown in Table 5 together with the results of Comparison Examples 2 and 5.

COMPARISON EXAMPLES 9 TO 11

By following the same procedures as Examples 32, 34, and 35 except that the coumarin compounds were not added, each of electrophotographic light-sensitive materials was prepared and the density difference was evaluated on each sample by the same manner as in Example 1.

TABLE 4

| | Coumarine Compound | | Potential | 1 Cycle (V) | 100 Cycles (V) | Density difference of prints between A4 paper passed portion and non-passed portions after printing 500 prints |
|---|---|---|---|---|---|---|
| | No. | Amount (equivalent) | | | | |
| Example 22 | I'-1 | 0.2 | VH | −306 | −305 | No difference |
| | | | VL | −77 | −75 | " |
| Example 23 | I'-1 | 0.01 | VH | −308 | −302 | " |
| | | | VL | −85 | −78 | " |
| Example 24 | I'-1 | 0.1 | VH | −307 | −305 | " |
| | | | VL | −83 | −80 | " |
| Example 25 | I'-1 | 1.0 | VH | −300 | −299 | " |
| | | | VL | −70 | −68 | " |
| Example 26 | I'-1 | 2.0 | VH | −298 | −296 | " |
| | | | VL | −68 | −67 | " |
| Example 27 | I'-1 | 4.0 | VH | −285 | −284 | " |
| | | | VL | −54 | −52 | " |
| Example 28 | I'-2 | 0.2 | VH | −301 | −299 | " |
| | | | VL | −67 | −65 | " |
| Example 29 | I'-5 | 0.2 | VH | −309 | −309 | " |
| | | | VL | −78 | −79 | " |
| Example 30 | I'-11 | 0.2 | VH | −304 | −303 | " |
| | | | VL | −75 | −72 | " |
| Comparison Example 1 | — | — | VH | −310 | −278 | The density is higher at the A4 paper non-passed portions than the passed portion |
| | | | VL | −89 | −58 | |

EXAMPLES 31 TO 35

By following the same procedure as Example 22 except that the compounds shown in Table 5 below The results obtained are shown in Table 5.

TABLE 5

| | Pigment No. | Coumarine Compound | Potential | 1 Cycle (V) | 100 Cycles (V) | Density difference of print between A4 paper passed portion and non-passed portions after printing 500 prints |
|---|---|---|---|---|---|---|
| Example 31 | ε-Type Copper Phthalocyanine | I'-4 | VH | −301 | −299 | No difference |
| | | | VL | −68 | −65 | " |
| Example 32 | II-6 | I'-2 | VH | −306 | −301 | " |
| | | | VL | −87 | −81 | " |
| Example 33 | II-10 | I'-11 | VH | −305 | −302 | " |
| | | | VL | −90 | −85 | " |
| Example 34 | II-12 | I'-11 | VH | −300 | −298 | " |
| | | | VL | −85 | −83 | " |
| Example 35 | II-20 | I'-5 | VH | −301 | −297 | " |
| | | | VL | −86 | −81 | " |
| Comparison Example 2 | ε-Type Copper Phthalocyanine | — | VH | −304 | −271 | The density of higher at the A4 paper non-passed portions than the passed portion |
| | | | VL | −75 | −49 | |
| Comparison Example 9 | II-6 | — | VH | −308 | −277 | The density of higher at the A4 paper non-passed portions than the passed portion |
| | | | VL | −94 | −71 | |
| Comparison Example 5 | II-10 | — | VH | −310 | −286 | The density of higher at the A4 paper non-passed portions than the passed portion |
| | | | VL | −97 | −77 | |

TABLE 5-continued

|  | Pigment No. | Coumarine Compound | Potential | 1 Cycle (V) | 100 Cycles (V) | Density difference of print between A4 paper passed portion and non-passed portions after printing 500 prints |
|---|---|---|---|---|---|---|
| Comparison Example 10 | II-12 | — | VH<br>VL | −303<br>−87 | −270<br>−66 | The density of higher at the A4 paper non-passed portions than the passed portion |
| Comparison Example 11 | II-20 | — | VH<br>VL | −302<br>−92 | −279<br>−70 | The density of higher at the A4 paper non-passed portions than the passed portion |

EXAMPLES 36 TO 39

By following the same procedure as Example 22 except that a perylene pigment (Compound IV-1) was used as a charge generating pigment and each of the compounds shown in Table 6 below was used in place of the coumarin compound each of electrophotographic light-sensitive materials was prepared. Then, the density difference was evaluated on each sample as in Example 22 except that a halogen lamp (filtered by an interference filter having a central wavelength of 550 nm., and the exposure amount was set to 20 erg/cm$^2$) was used as the light source.

The results obtained are shown in Table 6 together with the result in Comparison Example 7.

TABLE 6

| | Pigment No. | Coumarine Compound No. | Potential | 1 Cycle (V) | 100 Cycles (V) |
|---|---|---|---|---|---|
| Example 36 | IV-1 | I'-1 | VH<br>VL | −326<br>−127 | −325<br>−124 |
| Example 37 | IV-1 | I'-2 | VH<br>VL | −323<br>−122 | −320<br>−121 |
| Example 38 | IV-1 | I'-5 | VH<br>VL | −329<br>−131 | −328<br>−128 |
| Example 39 | IV-1 | I'-11 | VH<br>VL | −326<br>−127 | −325<br>−122 |
| Comparison Example 7 | IV-1 | — | VH<br>VL | −331<br>−160 | −300<br>−132 |

EXAMPLE 40

By following the same procedure as Example 22 except that an aluminum pipe having an outside diameter of 84 mm and a length of 340 mm, the surface of which has been subjected to a mirror plane polishing treatment, was used as the base material, an electrophotographic light-sensitive material was prepared.

The electrophotographic light-sensitive material thus prepared was mounted on the two-color laser printer as used in Example 21, 500 prints each having a pattern having a mixture of red and black images were printed using B4 size papers, and the change of the printout densities at the red portion and the black portion was observed.

The result showed that clear printouts each having no background fog at both the red portion and the black portion was obtained.

As described above, the electrophotographic light-sensitive material has the charge generating layer comprising a binder resin containing the positive hole-transferring charge generating pigment and the compound shown by the aforesaid formula (I) as described above and hence has excellent effects that the light sensitivity is high and the potentials at the exposed portions and unexposed portions are stable without being reduced even in the case of copying a large number of prints as compared to the case of not containing the compound of formula (I) in the charge generating layer.

The electrophotographic light-sensitive material is suitable for an electrophotographic image-forming process of repeating the steps of uniform negative charging, imagewise exposure, reversal development, positive charge transferring, and charge elimination, for example, for a laser printer, etc. In this case, the surface potential of the light-sensitive material in the image exposure is always kept at a stable potential from the initial image-forming operation after repeating the image-forming steps many times, without causing the reduction of the surface potential with the repeat of the image-forming step, whereby images having stable image density can be obtained and also the occurrence of fog can be restrained.

Also, when transfer papers are changed to papers having a wider size after repeating the image-forming step many times using transfer papers of narrow size, the transfer density does not high at the portions corresponding to the width difference of the transfer papers and hence images having no fog at the background portions and uniform density can be obtained.

When the charge generating layer does not contain the aforesaid compound of formula (I), the surface potentials of the exposed portions and the unexposed portions are gradually reduced with the repeat of the image-forming operation, the image density is gradually increased, and fog forms at the background portions. Also, when the transfer papers are changed to papers having a wider size after repeating the image-forming step many times using transfer papers of a narrow size, the increase of the image density and the formation of fog at the background portions are observed at the portions corresponding to the width difference of the transfer papers.

Furthermore, the electrophotographic light-sensitive material of this invention can be applied to a so-called one-pass multicolor image-forming process.

While the invention has been described in detail and with reference to specific embodiments thereof, it will be apparent to one skilled in the art that various changes and modifications can be made therein without departing from the spirit and scope thereof.

What is claimed is:

1. An electrophotographic light-sensitive material comprising a conductive support having formed thereon, in succession, a charge generating layer and a charge transfer layer, wherein the charge generating layer comprises a binder resin containing therein a positive hole-transferring charge generating pigment and a compound represented by formula (I)

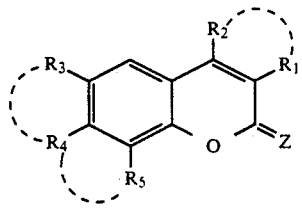 (I)

wherein Z represents

or an oxygen atom; $R_1$ represents a hydrogen atom, an alkyl group, —CN, —COOH, —COOR$_6$ (wherein $R_6$ represents an alkyl group), an aryl group,

(wherein A represents an oxygen atom or a sulfur atoms), or

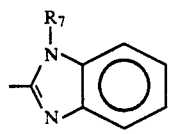

(wherein $R_7$ represents an alkyl group); $R_2$ represents a hydrogen atom, an alkyl group, or a halogenated alkyl group; $R_3$ represents a hydrogen atom or an alkyl group; $R_4$ represents a hydrogen atom, an alkyl group, —OH, —NH$_2$, —NHR$_8$ (wherein $R_8$ represents an alkyl group) or —NR$_9$R$_{10}$ (wherein $R_9$ and $R_{10}$ each represents an alkyl group); and $R_5$ represents a hydrogen atom or an alkyl group; said $R_1$ and $R_2$ may combine with each other to form a ring and two or three of $R_3$, $R_4$, and $R_5$ may combine with each other to form a ring.

2. The electrophotographic light-sensitive material according to claim 1, wherein Z in formula (I) is

3. The electrophotographic light-sensitive material according to claim 1, wherein Z is an oxygen atom.

4. The electrophotographic light-sensitive material according to claim 1, wherein the charge generating layer contains the compound shown by formula (I) in an amount of from 0.01 to 2 equivalents to the positive hole-transferring charge generating pigment.

5. The electrophotographic light-sensitive material according to claim 1, wherein the positive hole-transferring charge generating pigment is a phthalocyanine series pigment, a squarylium series pigment or a perylene series pigment.

6. An image-forming process which comprises uniformly negatively charging the surface of the electrophotographic light-sensitive material described in claim 1, imagewise exposing the light-sensitive material to form electrostatic latent images, attaching a negatively charged toner to the low potential portions of the electrostatic latent images to form toner images, superposing a transfer material on the electrophotographic light-sensitive material having the toner images, applying positive charges thereto from the back surface of the transfer material, and, thus, transferring the toner images onto the transfer material.

7. An image-forming process which comprises uniformly negatively charging the surface of the electrophotographic light-sensitive material described in claim 1, applying thereto a 1st imagewise exposure to form a 1st electrostatic latent image, attaching a negatively charged toner to the low potential portions of the 1st electrostatic latent images to form a 1st toner image, applying thereto a 2nd imagewise exposure to form a 2nd electrostatic latent image, attaching a positively charged 2nd toner to the high potential portions of the 2nd electrostatic latent images to form a 2nd toner image, making the polarities of the 1st and 2nd toner images equal to one of the polarities, superposing a transfer material on the electrophotographic light-sensitive material having the 1st and 2nd toner images, applying thereto charges having the opposite polarity to the polarity of the 1st and 2nd toner images from the back surface of the transfer material, and thus, transferring the 1st and 2nd toner images onto the transfer material.

* * * * *